(12) United States Patent
Bettuchi

(10) Patent No.: US 8,951,282 B2
(45) Date of Patent: *Feb. 10, 2015

(54) EXTRALUMINAL SEALANT APPLICATOR AND METHOD

(71) Applicant: Covidien LP, Mansfield, MA (US)

(72) Inventor: Michael J. Bettuchi, Middletown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/917,796

(22) Filed: Jun. 14, 2013

(65) Prior Publication Data

US 2013/0282055 A1 Oct. 24, 2013

Related U.S. Application Data

(60) Continuation of application No. 13/152,625, filed on Jun. 3, 2011, now Pat. No. 8,480,705, which is a division of application No. 12/001,625, filed on Dec. 11, 2007, now Pat. No. 7,972,357, which is a continuation of application No. 11/251,118, filed on Oct. 14, 2005, now Pat. No. 7,744,624.

(60) Provisional application No. 60/620,018, filed on Oct. 18, 2004.

(51) Int. Cl.
| | | |
|---|---|---|
| *A61B 17/08* | (2006.01) | |
| *A61B 17/00* | (2006.01) | |
| *A61B 17/11* | (2006.01) | |
| *A61B 17/064* | (2006.01) | |

(52) U.S. Cl.
CPC .......... *A61B 17/00491* (2013.01); *A61B 17/08* (2013.01); *A61B 17/11* (2013.01); *A61B 17/064* (2013.01); *A61B 2017/1125* (2013.01)
USPC ........................................................ 606/207

(58) Field of Classification Search
USPC .......................... 606/153, 205–208, 213–215
See application file for complete search history.

(56) References Cited

U.S. PATENT DOCUMENTS

| | | | |
|---|---|---|---|
| 1,852,542 | A | 4/1932 | Sovatkin |
| 3,079,606 | A | 3/1963 | Bobrov et al. |
| 3,101,715 | A | 8/1963 | Glassman |
| 3,223,083 | A | 12/1965 | Cobey |

(Continued)

FOREIGN PATENT DOCUMENTS

| | | |
|---|---|---|
| EP | 0 577 373 | 1/1994 |
| JP | H06 327684 A | 11/1994 |

(Continued)

OTHER PUBLICATIONS

U.S. Appl. No. 13/889,646, filed Jun. 18, 2013, Bettuchi.

(Continued)

*Primary Examiner* — Ryan Severson

(57) ABSTRACT

An apparatus for applying sealant to a target tissue of a surgical site is provided. The apparatus includes a handle, conduit and an end effector. The handle has means configured and adapted for operating the end effector and dispensing biological sealant to the surgical site via the end effector. The conduit stores and/or carries sealant towards the end effector. The end effector is configured to clamp around a body organ or tissue and apply and confine biological sealant in a substantially uniform manner thereto.

7 Claims, 8 Drawing Sheets

(56) References Cited

U.S. PATENT DOCUMENTS

| | | |
|---|---|---|
| 3,490,675 A | 1/1970 | Green et al. |
| 3,499,591 A | 3/1970 | Green |
| 3,777,760 A | 12/1973 | Essner |
| 3,980,086 A | 9/1976 | Kletschka et al. |
| 4,429,695 A | 2/1984 | Green |
| 4,873,977 A | 10/1989 | Avant et al. |
| 5,065,929 A | 11/1991 | Schulze et al. |
| 5,141,516 A | 8/1992 | Detweiler |
| 5,156,613 A | 10/1992 | Sawyer |
| 5,156,614 A | 10/1992 | Green et al. |
| 5,254,113 A | 10/1993 | Wilk |
| 5,318,531 A | 6/1994 | Leone |
| 5,392,979 A | 2/1995 | Green et al. |
| 5,417,709 A | 5/1995 | Slater |
| 5,465,896 A | 11/1995 | Allen et al. |
| 5,542,594 A | 8/1996 | McKean et al. |
| 5,554,119 A | 9/1996 | Harrison et al. |
| 5,611,775 A | 3/1997 | Machold et al. |
| 5,669,934 A | 9/1997 | Sawyer |
| 5,690,675 A | 11/1997 | Sawyer et al. |
| 5,749,895 A | 5/1998 | Sawyer et al. |
| 5,799,857 A | 9/1998 | Robertson et al. |
| 5,824,015 A | 10/1998 | Sawyer |
| 5,843,033 A | 12/1998 | Ropiak |
| 5,866,561 A | 2/1999 | Ungs |
| 5,895,412 A | 4/1999 | Tucker |
| 5,915,616 A | 6/1999 | Viola et al. |
| 5,931,165 A | 8/1999 | Reich et al. |
| 5,964,394 A | 10/1999 | Robertson |
| 5,989,268 A | 11/1999 | Pugsley et al. |
| 6,032,849 A | 3/2000 | Mastri et al. |
| 6,045,560 A | 4/2000 | McKean et al. |
| 6,149,641 A | 11/2000 | Ungs |
| 6,165,201 A | 12/2000 | Sawhney |
| 6,179,862 B1 | 1/2001 | Sawhney |
| 6,228,051 B1 | 5/2001 | Trumbull |
| 6,287,323 B1 | 9/2001 | Hammerslag |
| 6,398,797 B2 | 6/2002 | Bombard et al. |
| 6,451,029 B1 | 9/2002 | Yeatman |
| 6,488,197 B1 | 12/2002 | Whitman |
| 6,491,201 B1 | 12/2002 | Whitman |
| 6,623,452 B2 | 9/2003 | Chien et al. |
| 6,681,979 B2 | 1/2004 | Whitman |
| 6,692,491 B1 | 2/2004 | Phan |
| 6,695,199 B2 | 2/2004 | Whitman |
| 2001/0007069 A1 | 7/2001 | Bombard et al. |
| 2002/0010482 A1 | 1/2002 | Watt |
| 2002/0026159 A1 | 2/2002 | Zhu et al. |
| 2002/0049454 A1 | 4/2002 | Whitman et al. |
| 2002/0156150 A1 | 10/2002 | Williams et al. |
| 2002/0165562 A1 | 11/2002 | Grant et al. |
| 2002/0173558 A1 | 11/2002 | Williams et al. |
| 2003/0050590 A1 | 3/2003 | Kirsch |
| 2003/0073981 A1 | 4/2003 | Whitman et al. |
| 2003/0073982 A1 | 4/2003 | Whitman |
| 2003/0089757 A1 | 5/2003 | Whitman |
| 2003/0111507 A1 | 6/2003 | Nunez |
| 2003/0236518 A1 | 12/2003 | Marchitto et al. |
| 2004/0059283 A1 | 3/2004 | Kirwan et al. |
| 2004/0092960 A1 | 5/2004 | Abrams et al. |
| 2004/0093029 A1 | 5/2004 | Zubik et al. |
| 2005/0038471 A1 | 2/2005 | Chan et al. |
| 2005/0043678 A1 | 2/2005 | Freyman et al. |

FOREIGN PATENT DOCUMENTS

| | | |
|---|---|---|
| WO | WO 00/56376 | 9/2000 |
| WO | WO 01/62158 | 8/2001 |
| WO | WO 01/62162 | 8/2001 |
| WO | WO 02/30297 | 4/2002 |
| WO | 03/088845 A2 | 10/2003 |
| WO | WO 03/088844 | 10/2003 |
| WO | WO 03/094743 | 11/2003 |
| WO | WO 03/094746 | 11/2003 |
| WO | WO 03/105698 | 12/2003 |

OTHER PUBLICATIONS

European Search Report dated Nov. 25, 2014 issued in European Appln. No. 05 81 1931.

EXTRALUMINAL SEALANT APPLICATOR AND METHOD

CROSS-REFERENCE TO RELATED APPLICATION

This application is a Continuation application claiming the benefit of and priority to U.S. patent application Ser. No. 13/152,625, filed on Jun. 3, 2011, now U.S. Pat. No. 8,480,705, which is a Divisional application claiming the benefit of and priority to U.S. patent application Ser. No. 12/001,625, filed on Dec. 11, 2007, now U.S. Pat. No. 7,972,357, which is a Continuation application claiming the benefit of and priority to U.S. patent application Ser. No. 11/251,118, filed on Oct. 14, 2005, now U.S. Pat. No. 7,744,624, which claims the benefit of and priority to U.S. Provisional Application Ser. No. 60/620,018, filed on Oct. 18, 2004, the disclosure of each of the above-identified applications being hereby incorporated by reference in their entirety.

BACKGROUND

1. Technical Field

The present disclosure relates to surgical instruments and methods for enhancing properties of tissue repaired or joined by surgical staples and, more particularly to surgical instruments and methods designed to apply and confine a non-mechanical biocompatible wound closure material to enhance the properties of repaired or adjoined tissue at a target surgical site.

2. Background of Related Art

Throughout the years the medical field has utilized various techniques in an effort to join or bond body tissue together. Historically, suturing was the accepted technique for rejoining severed tissues and closing wounds. Suturing was historically achieved with a surgical needle and a suturing thread, and more recently, with a variety of polymeric or metallic staples, as will be discussed below. The intended function of sutures is to hold the edges of a wound or tissue against one another during the healing process so as to reduce discomfort, pain, scarring and the time required for healing.

Staples have recently been used to replace suturing when joining or anastomosing various body structures, such as, for example, the bowel or bronchus. The surgical stapling devices employed to apply these staples are generally designed to simultaneously cut and seal an extended segment of tissue in a patient, thus vastly reducing the time and risks of such procedures.

Linear or annular surgical stapling devices are employed by surgeons to sequentially or simultaneously apply one or more linear rows of surgical fasteners, e.g., staples or two-part fasteners, to body tissue for the purpose of joining segments of body tissue together and/or for the creation of anastomosis. Linear surgical stapling devices generally include a pair of jaws or finger-like structures between which body tissue to be joined is placed. When the surgical stapling device is actuated and/or "fired," firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples. Examples of such linear surgical stapling devices are Models "GIA™" and "Endo GIA™" instruments available from United States Surgical, a Division of Tyco Health-Care Group, LP, Norwalk, Conn. and disclosed in, inter alia, U.S. Pat. No. 5,465,896 to Allen et al., the entire contents of which is incorporated herein by reference.

Annular surgical stapling devices generally include an annular staple cartridge assembly including a plurality of annular rows of staples, typically two, an anvil assembly operatively associated with the annular cartridge assembly, and an annular blade disposed internal of the rows of staples.

Another type of surgical stapler is an end-to-end anastomosis stapler. An example of such a device is a Model "EEA™" instrument available from United States Surgical, a Division of Tyco Health-Care Group, LP, Norwalk, Conn. and disclosed in, inter alia, U.S. Pat. No. 5,392,979 to Green et al., the entire contents of which is incorporated herein by reference. In general, an end-to-end anastomosis stapler typically places an array of staples into the approximated sections of a patient's bowels or other tubular organs. The resulting anastomosis contains an inverted section of bowel which contains numerous "B" shaped staples to maintain a secure connection between the approximated sections of bowel.

In addition to the use of surgical staples, sealants, e.g., biological sealants, can be applied to the surgical site to guard against leakage. Typically, the biological sealants are manually applied to the outer surface of the staple line by a physician by spraying on, brushing on, swabbing on, or any combinations thereof. This manual application of biological sealant can lead to non-uniformity of the thickness of sealant across the staple line and/or omitting a portion of the intended coverage area due to inability to see or reach the desired location.

A need exists for surgical apparatus or structure for applying wound treatment material to an exterior surface of tissue to bond tissue, guard against leakage and the like.

SUMMARY

The present disclosure relates to surgical instruments and a method for applying an adhesive or sealant to an anastomosis site after the site has been surgically stapled and for confining the sealant to the desired location. As used herein, sealant is intended to encompass a broad range of biologically compatible materials including tissue adhesive, tissue sealing compositions, etc.

The present extraluminal sealant applicator includes a handle, a shaft and an end effector, such as a clamp. The handle has means configured and adapted for operating the end effector and dispensing biological sealant to the surgical site via the end effector. The shaft contains conduit therein or thereon for storing sealant and/or carrying sealant towards the end effector. The end effector is configured to clamp around a body organ or tissue and apply and confine biological sealant in a substantially uniform manner thereto.

An apparatus is disclosed for applying sealing to a target tissue of a surgical site. The apparatus comprises a handle, an end effector and at least one conduit for conveying sealant The end effector includes a sealant-applying structure for applying sealant to the target tissue. The conduit conveys sealant to the sealant-applying structure in the end effector.

In one embodiment, the end effector is in the form of a clamp, which may comprise two jaw members.

The apparatus may also include a shaft extending between the handle and the end effector. The shaft defines a longitudinal axis.

It is envisioned for each of the jaw members to be arcuate or planar with respect to the longitudinal axis.

Each of the jaw members may be rigid or deformable. It is contemplated that one jaw member is rigid and the other jaw member is deformable.

In an embodiment, at least one of the jaw members includes at least one reservoir.

It is contemplated for at least one of the jaw members to comprise side walls, which confine sealant. Each side wall includes a first end operatively connected to the jaw member and a second end extending from the jaw member to come into contact with tissue when the end effector is in a closed condition. At least one side wall may comprise elements for increasing friction between the second end of the side wall and tissue. It is envisioned that the elements for increasing friction are pins. The side walls may be rigid or flexible.

It is envisioned for the end effector to comprise a locking means for maintaining the end effector in a closed condition.

In an embodiment, the shaft comprises at least one conduit extending therethrough for carrying sealant from the handle to the sealant-applying structure of the end effector.

It is envisioned for the handle to comprise means for locking the end effector in a closed condition. The handle may also include a structure, such as a sliding mechanism or a lever, for controllably operating the end effector.

The sealant-applying structure of the present disclosure may be, for example, a lever or a sliding mechanism.

The present disclosure also includes a method for applying sealant to a target tissue site. The method includes the steps of providing an apparatus having a clamp; positioning the clamp around and closing the clamp on the target tissue site; and applying sealant to the target tissue site via the clamp.

In one embodiment, the present disclosure includes an apparatus for applying sealant to a target tissue site. The apparatus comprises an end effector, side walls and a conduit. The end effector is operatively configured to be able to substantially surround the target tissue site. The side walls confine sealant. The conduit is in fluid association with the end effector and conveys sealant to the end effector for dispensing onto the target tissue site. The end effector may include two jaw members, which may be configured to releasably lock with each other when the end effector is positioned around the target tissue site.

The apparatus and method of the present disclosure may be implemented after an anastomosis procedure where a body organ, such as an intestine, bronchus or bowel, is surgically stapled using an end-to-end anastomosis stapler or other suitable device. After such a procedure, the disclosed apparatus is positioned near the staple line of the tissue, with the clamp in an open position. A user then closes the clamp around the organ by using a clamping means, such as a trigger, button, sliding device, etc., which may be disposed on the handle of the apparatus. It is envisioned for the clamping means to both close and open the clamp. After the clamp is closed, the user applies the biological sealant to the desired clamped location by using a sealant-applying structure, such as a trigger, button, sliding device, etc., which may be disposed on the handle of the apparatus. Once the sealant is applied to the surgical site, the user of the disclosed apparatus may continue to maintain the clamp in a closed position until the sealant has sufficiently cured. After sufficient curing has taken place, the user may open the clamp using the clamping means and remove the apparatus from the patient's body.

The extraluminal sealant applicator may further include a locking means disposed on the clamp, e.g., the distal portion of the clamp, to maintain the clamp in a closed position around the body organ or tissue. In addition, a locking means may be located on the handle of the apparatus for locking the clamp in a desired position.

The extraluminal sealant applicator of the present disclosure may further include a sealant confining structure, e.g., side walls, gaskets, etc., disposed on one or both sides of each jaw member. The side walls, being either rigid or flexible, may extend from the jaw member inwardly and come into contact with the body organ or tissue when the clamp is in a closed position. The side walls may help to confine the sealant to the surgical site, thus preventing or minimizing the spreading of the sealant to other parts of the body.

According to one embodiment of the present disclosure, it is envisioned that a clamp alone may be provided for clamping a body organ or tissue and for applying sealant. In this embodiment, a user places the clamp around the organ and closes the clamp. It is also envisioned that the clamp has parallel or pivotal jaw members and is designed and configured for use on a linear staple line. The user may then use means disposed on the clamp or an external means to apply the biological sealant to the tissue. Means for applying biological sealant disposed on the clamp can include a switch, button or slide to release biological sealant from within the clamp, through openings within the clamp, and onto the tissue. External means, such as a syringe, can be used to inject the clamp with a biological sealant solution that would be applied to the tissue through openings within the clamp. Side walls may be disposed on the jaw members to confine the sealant to the desired location.

A method of the present disclosure includes the steps of placing an end effector or clamp near an anastomosis site; closing the end effector or clamp to substantially surround the perimeter of the body organ to be sealed; applying biological sealant to the anastomosis site via the end effector or clamp; allowing time for the biological sealant to cure or partially cure; opening the end effector or clamp; and removing the apparatus from the patient.

According to an embodiment of the present disclosure, it is envisioned that the end effector may be configured to apply sealant to a surgical site that has been linearly stapled.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein.

DETAILED DESCRIPTION OF EMBODIMENTS

Figure 1:
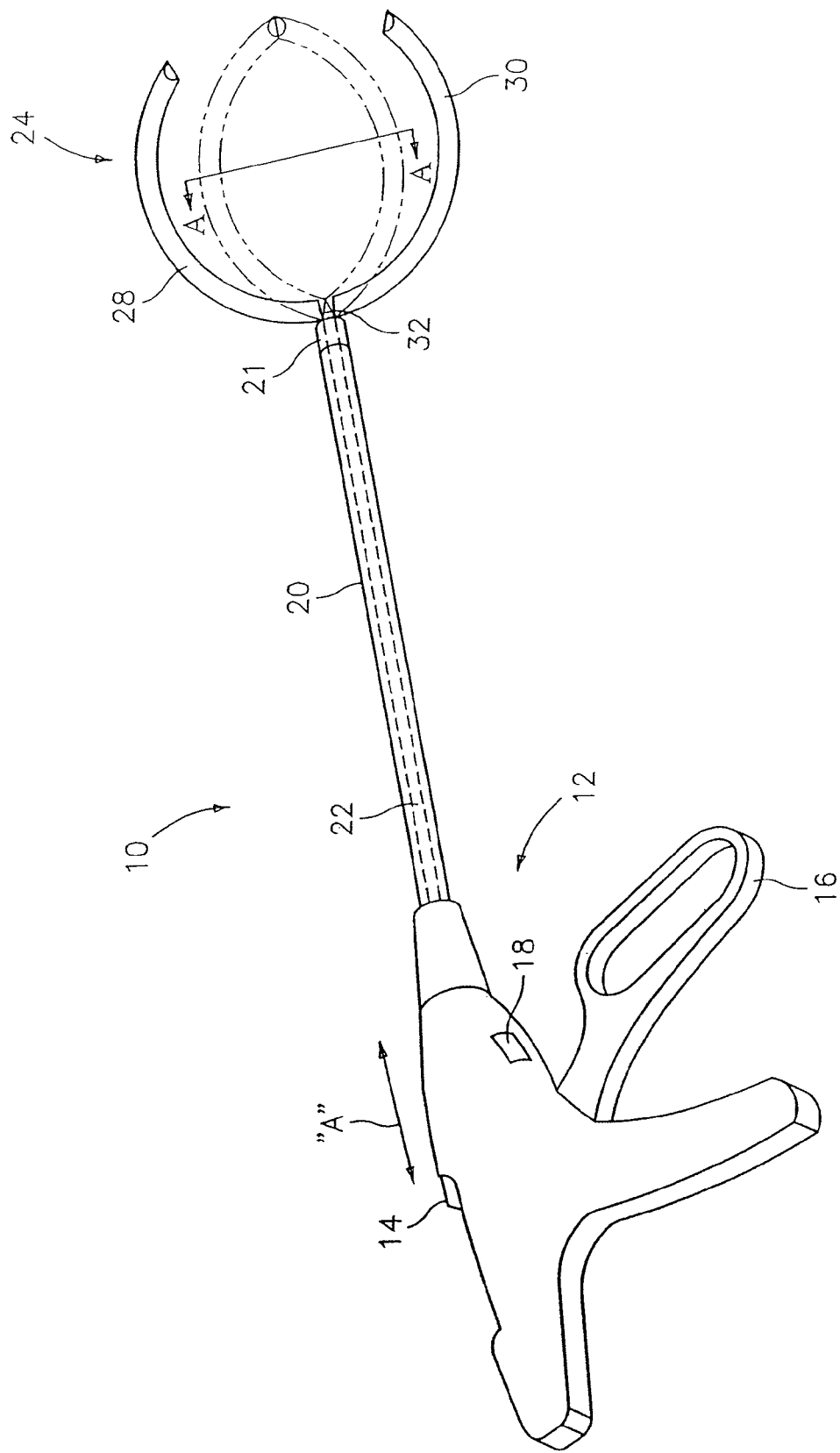
FIG. 1 is a perspective view of an extraluminal sealant applicator in accordance with the present disclosure.

Embodiments of the presently disclosed extraluminal sealant applicators will now be described in detail with reference to the drawing figures wherein like reference numerals identify similar or identical elements. As used herein and as is traditional, the term "distal" refers to that portion which is farthest from the user while the term "proximal" refers to that portion which is closest to the user.

Referring initially to FIG. 1, an extraluminal sealant applicator is generally designated as 10. The extraluminal sealant applicator 10 includes a handle member 12, a shaft 20 extending distally from the handle member 12, and an end effector 24 operatively supported on a distal end 21 of the shaft 20. As seen in FIG. 1, the handle member 12 includes end effector operating means 14, sealant-applying structure 16, and end effector locking means 18. The shaft 20 may carry one or more conduits 22 for transporting sealant 34 (shown in FIGS. 2 and 4) therethrough. The end effector 24, as shown in FIG. 1, may be in the form of a clamp and includes a first jaw member 28 and a second jaw member 30. It is envisioned that the end effector 24 is operatively connected to the distal end 21 of the shaft 20 by a hinge 32 or the like.

With continued reference to FIG. 1, the end effector operating means 14 may be a slider-type device operatively associated with handle member 12. In operation, as the end effector operating means 14 is slid in either a distal or proximal direction (as indicated by arrow "A"), the jaw members 28, 30 are actuated between open and closed positions. It is envisioned that the jaw members 28, 30 may close upon proximal movement of the end effector operating means 14 and open upon distal movement of the end effector operating means 14. It is also envisioned to have the jaw members 28, 30 open or close upon depression of a button, the flip of a switch, the depression of a handle or trigger, or any other reasonable means.

Figure 16:
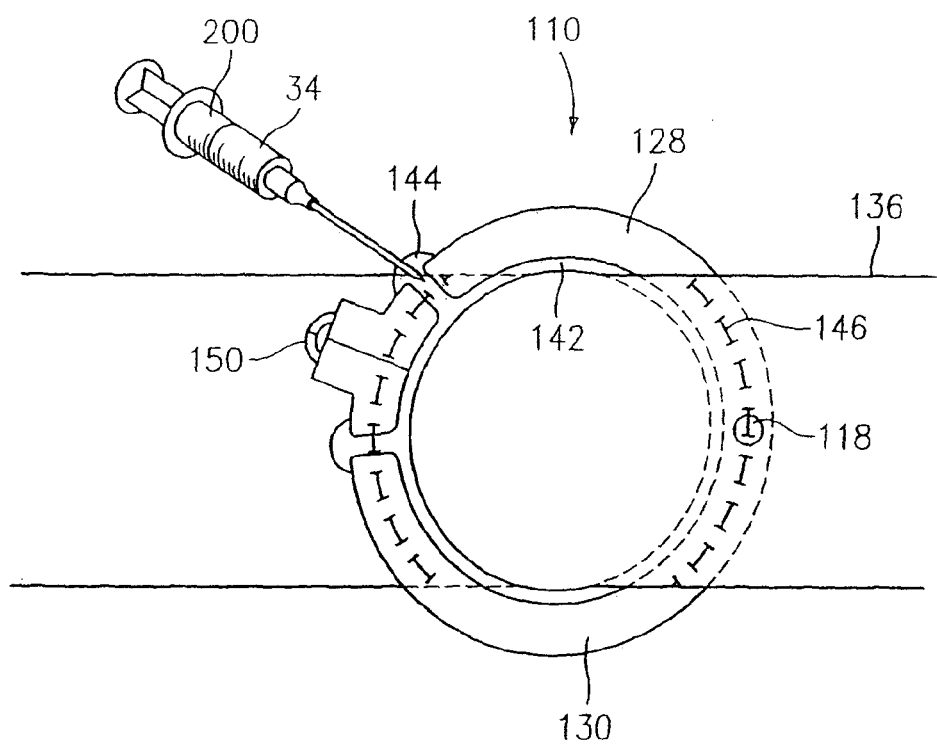
FIG. 16 is a perspective view of the clamp-type extraluminal sealant applicator of FIG. 15 depicted in a closed position around a body organ.

As seen in FIG. 1, the sealant-applying structure 16 may be in the form of a trigger operatively supported on the handle member 12. It is envisioned that in operation, depression of the trigger 16 pushes sealant 34 (shown in FIGS. 2 and 4), e.g., biological sealant, through the conduit 22 in the shaft 20 towards the end effector 24. It is contemplated to use a slider device, button, switch or any other reasonable means to dispense sealant 34 through the conduit 22 of the shaft 20 and towards the end effector 24. In an embodiment, sealant 34 may be introduced into the end effector 24 by an external means 200, such as, for example, by injection with a syringe (FIG. 16). The sealant 34 may be released from a reservoir (not shown) in or on the handle member 12. It is envisioned that the trigger 16 may cause the sealant 34 to be sprayed out of the end effector 24 on the distal end 21 of the shaft 20 onto a staple line or target tissue.

It is contemplated that the sealant 34 is any material for joining, healing, sealing or otherwise treating tissue. In an embodiment, the sealant 34 is a bio-compatible sealant and/or adhesive, including, and not limited, to sealants which cure upon tissue contact, sealants which cure upon exposure to ultraviolet (UV) light, sealants which are two-part systems which are kept isolated from one another and are combined or any combinations thereof. In one embodiment, it is contemplated that such sealants and/or adhesives are curable. For example, the sealants and/or adhesives may have a cure time of from about 10 to about 15 seconds may be used. In another embodiment, it is contemplated that a sealant 34 and/or adhesive having a cure time of about 30 seconds may be used. In some embodiments, the sealant 34 and/or adhesive is a bio-absorbable and/or bio-resorbable material.

In certain embodiments, the sealant 34 is a PEG-based material. Examples of classes of materials useful as the sealant 34 and/or adhesive include acrylate or methacrylate functional hydrogels in the presence of a biocompatible photoinitiator, alkyl-cyanoacrylates, isocyanate functional macromers with or without amine functional macromers, succinimidyl ester functional macromers with amine or sulfhydryl functional macromers, epoxy functional macromers with amine functional macromers, mixtures of proteins or polypeptides in the presence of aldehyde crosslinkers, Genipin, or water-soluble carbodiimides, anionic polysaccharides in the presence of polyvalent cations, etc. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc.

Surgical biocompatible sealants 34 which may be used in accordance with the present disclosure include adhesives whose function is to attach or hold organs, tissues or structures. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively.

Some specific materials which may be utilized as adhesives include isocyanate terminated hydrophilic urethane prepolymers derived from organic polyisocyanates and oxyethylene-based diols or polyols, including those disclosed in U.S. Pat. Nos. 6,702,731 and 6,296,607 and U.S. Published Patent Application No. 2004/0068078; alpha-cyanoacrylate based adhesives including those disclosed in U.S. Pat. No. 6,565,840; alkyl ester based cyanoacrylate adhesives including those disclosed in U.S. Pat. No. 6,620,846; adhesives based on biocompatible crosslinked polymers formed from water soluble precursors having electrophilic and nucleophilic groups capable of reacting and crosslinking in situ, including those disclosed in U.S. Pat. No. 6,566,406; two part adhesive systems including those based upon polyalkylene oxide backbones substituted with one or more isocyanate groups in combination with bioabsorbable diamine compounds, or polyalkylene oxide backbones substituted with one or more amine groups in combination with bioabsorbable diisoycanate compounds as disclosed in U.S. Published Patent Application No. 2003/0032734, the entire contents of which are incorporated by reference herein; and isocyanate terminated hydrophilic urethane prepolymers derived from aromatic diisocyanates and polyols as disclosed in U.S. Published Patent Application No. 2004/0115229, the entire contents of which are incorporated by reference herein. It is contemplated that any known suitable adhesive may be used.

In certain embodiments, the sealant 34 includes hemostats whose function is to halt or prevent bleeding. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc. Hemostats herein include astringents, e.g., aluminum sulfate, and coagulants.

It is envisioned that sealants 34 may be a relatively low viscosity fluid or liquid such that the sealant 34 may freely flow. It is further envisioned that the sealant 34 may include a fine powder of particulate material.

In other embodiments, sealants 34 may include a medicament. The medicament may include one or more medically and/or surgically useful substances such as drugs, enzymes, growth factors, peptides, proteins, dyes, diagnostic agents or hemostasis agents, monoclonal antibodies, or any other pharmaceutical used in the prevention of stenosis.

Sealant 34 may include visco-elastic film forming materials, cross-linking reactive agents, and energy curable adhesives. It is envisioned that an adhesive may be cured with the application of water and/or glycerin thereto. In this manner, the water and/or glycerin cure the adhesive and hydrate the wound.

It is further contemplated that the sealant 34 may include, for example, compositions and/or compounds which accelerate or beneficially modify the healing process when particles of the composition and/or compound are applied to or exposed to a surgical repair site. For example, the sealant 34 may be a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, sealant 34 may include one or several growth promoting factors, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

The end effector locking means 18 is depicted in FIG. 1 as a button that can be depressed for locking the end effector 24 in the closed position. It is contemplated by this disclosure that the end effector 24 is spring-biased to an open position. Accordingly, in use, once the end effector 24 is actuated to a closed position (shown as phantom lines in FIG. 1), the user can activate the locking means 18 to maintain the end effector 24 in the closed position. While the locking means 18 is depicted as a button on the handle member 12, it is envisioned that the locking means 18 can also be, for example, a lever, slider device or incorporated into the end effector operating means 14 as a ratchet-type trigger. It is also envisioned that a locking means 18 can be disposed on the distal end of each jaw member 28, 30 (shown in FIG. 2) such that the two locking means 18 engage each other when the end effector 24 is in a closed position. The different types of locking, means 18 envisioned by this present disclosure may be used individually or in conjunction with each other.

As seen in FIG. 1, the conduit 22 of the shaft 20 is shown as a single lumen or channel. It is contemplated that multiple conduits 22 can be disposed in the shaft 20. In an embodiment, two channels may be disposed in the shaft 20, wherein each conduit 22 supplies each of the two jaw members 28, 30 with sealant 34. Each of the two conduits 22 disposed in the shaft 20, can also be used for carrying one part of a two-part sealant, such that the two parts of the sealant mix with each other to form a sealant 34 prior to coming into contact with the body organ 36 or tissue (FIG. 2) or as they are dispensed from the jaw members 28, 30. It is also contemplated that four conduits 22 are disposed in the shaft 20, wherein two conduits 22 supply each jaw member 28, 30. As such, each part of a two-part sealant may be supplied to each of the two jaw members 28, 30. It is also contemplated to have any or all of the conduits 22 disposed on or along an external portion of the shaft 20, rather than inside the shaft 20.

Figure 2:
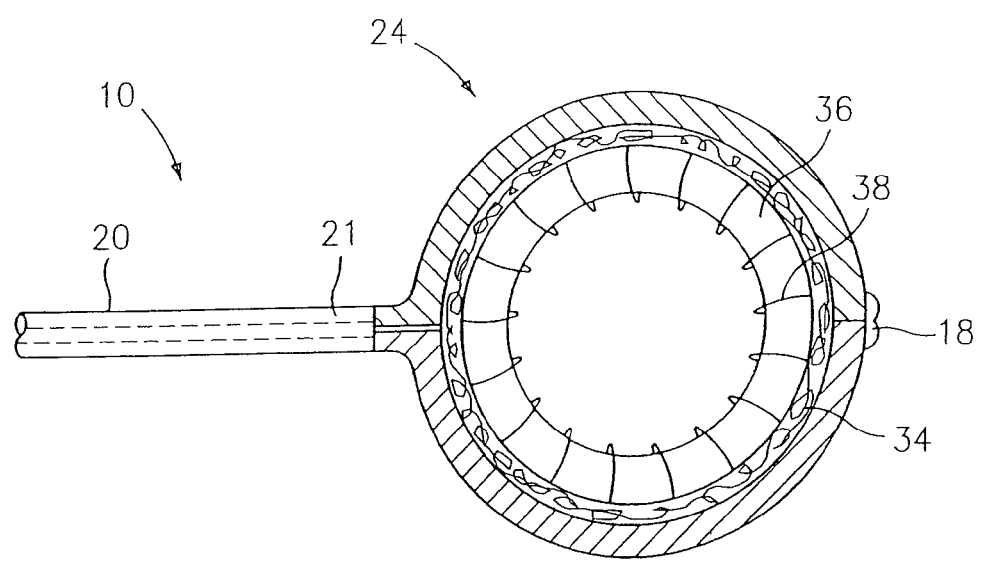
FIG. 2 is a perspective view of the distal portion of the end effector of the extraluminal sealant applicator of FIG. 1 depicted in a closed position around a body organ.
Figure 3:
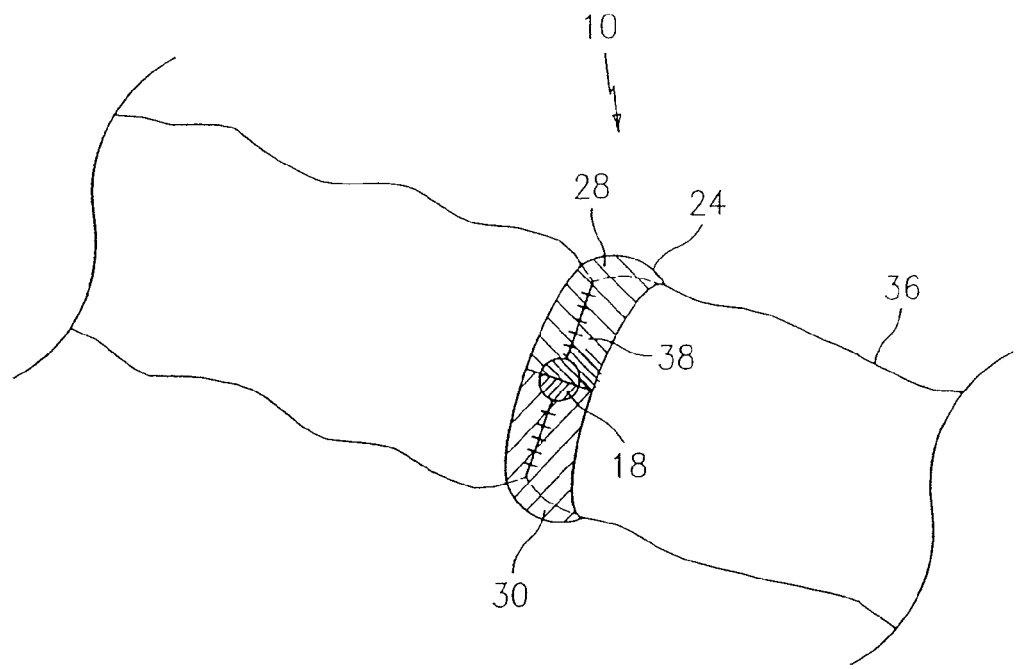
FIG. 3 is a longitudinal cross-sectional view of the end effector of the extraluminal sealant applicator of FIG. 1 depicted in a closed position around a body organ.
Figure 4:
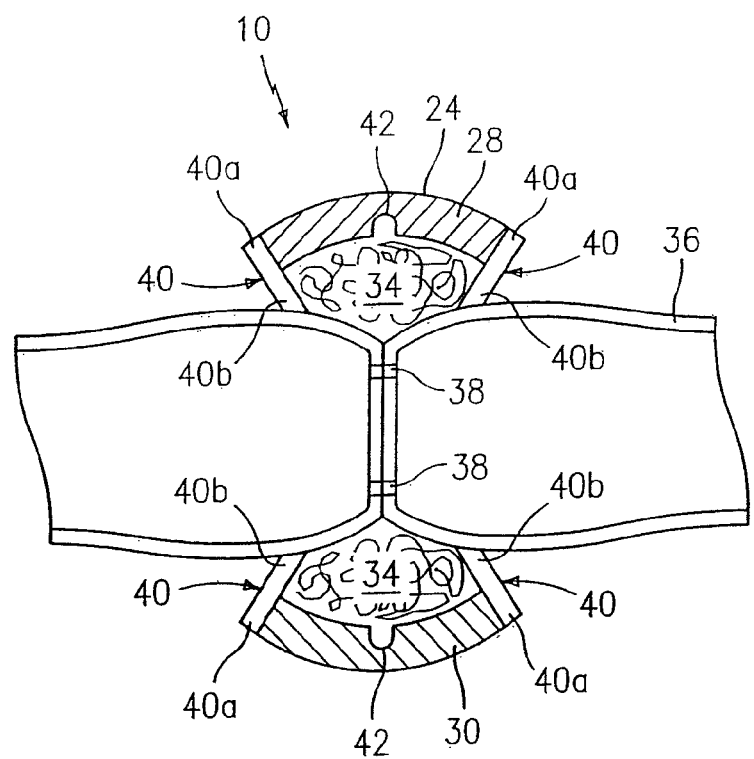
FIG. 4 is a cross-sectional view of the end effector of the extraluminal sealant applicator of FIG. 1, as taken through A-A of FIG. 1.
Figure 17:
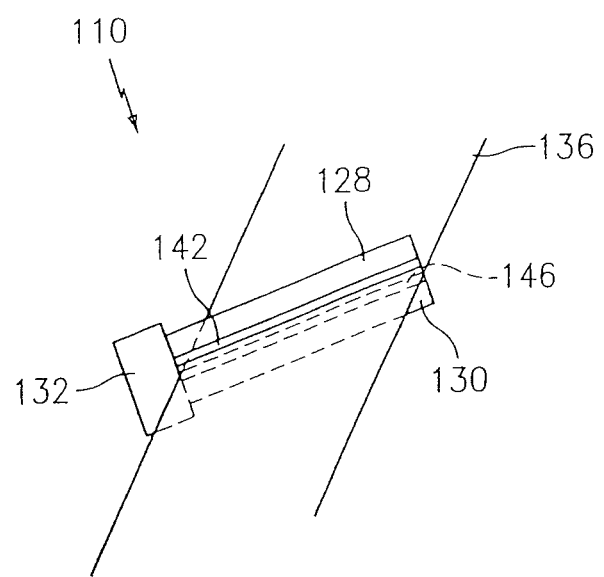
FIG. 17 is a perspective view of a clamp-type extraluminal sealant applicator for use with a linear stapling device depicted in a closed position on tissue.

Turning now to FIGS. 2-4, the end effector 24 of the extraluminal sealant applicator 10 is shown closed around a body organ 36. For example, the body organ 36 may be a bronchus, bowel, intestine, etc. or any other part of the body that has been joined by linear stapling (FIG. 17). As seen in FIGS. 2-4, the body organ 36 is depicted after a stapling procedure using an end-to-end anastomosis stapler has taken place. During such a procedure, surgical staples 38 are commonly used to join two sections of the body organ 36.

As seen in FIGS. 3 and 4, a layer of sealant 34 has been dispensed between the end effector 24 and the body organ 36. Sealant 34 at least substantially surrounds, preferably completely surrounds, the perimeter of the body organ 36 and seals any holes or tears (not shown) created by each surgical staple 38, any gaps that might exist between adjacent surgical staples 38, and the junction between the adjacent tissues to strengthen the bond therebetween.

As seen in FIGS. 2 and 3, the jaw members 28, 30 are depicted in a closed position around the body organ 36 and are locked together via locking means 18.

As seen in FIG. 4, a pair of sealant confining structures, e.g., side walls 40, is provided on or extends from both sides of each jaw member 28, 30 and extends the length thereof. The side walls 40 are configured and adapted to retain sealant 34 in close proximity to and overlying surgical staples 38 in order to keep sealant 34 from spreading away from the row of surgical staples 38. A first end 40a of each side wall 40 is operatively connected to each jaw member 28, 30, and a second end 40b of each side wall extends radially inwardly such that the second end 40b of the side wall 40 makes contact with the body organ 36 when the end effector 24 is in the closed position.

Figure 5:
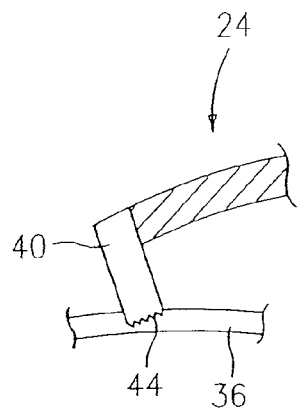
FIGS. 5-7 are enlarged cross-sectional views of portions of the end effector of the extraluminal sealant applicator of FIG. 1, illustrating different types of side walls.
Figure 6:
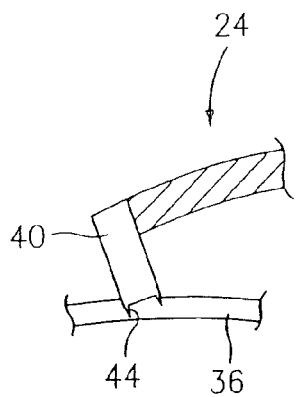
Figure 7:
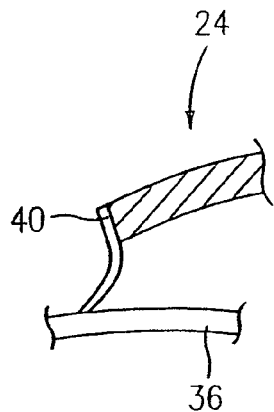

It is within the scope of the present disclosure for the side walls 40 of the end effector 24 to be made from either a rigid material (FIGS. 5 and 6), a flexible material (FIG. 7), or some combination thereof. As is to be appreciated, the side walls 40, which are flexible, substantially conform to the contours of the body organ 36. It is envisioned that the second end 40b of the side walls 40 may contain friction increasing elements 44 to increase friction between the second end 40b of the side wall 40 and the body organ 36, as illustrated in FIGS. 5 and 6. It is envisioned that such friction increasing elements 44 can be a series a detents (see FIG. 5), one or more pins (see FIG. 6), any combination thereof, or any other reasonable means to increase friction between the second end 40b of the side wall 40 and the body organ 36. Friction increasing elements 44 may help maintain the end effector 24 in place when in contact with the body organ 36.

Referring again to FIG. 4, at least one reservoir 42 is formed in each jaw member 28, 30 for holding and/or dispensing sealant 34 to the target tissue site. Reservoir 42 may be in the form of a channel extending at least partially around or along the jaw members 28, 30. The reservoir 42 is in fluid communication with the conduit 22 for receiving the sealant 34 therefrom. As seen in FIG. 4, the sealant 34 has been released or dispensed from the reservoir 42, substantially surrounds the body organ 36 and substantially covers the surgical site and the surgical staples 38 located therearound. The side walls 40 of the jaw members 28, 30 may help confine sealant 34 to the target tissue site. The end effector 24 is removed from the body organ 36 once the sealant 34 has fully or partially cured.

It is envisioned that the shape of the reservoir 42 is such that the end effector 24 and the jaw members 28, 30 thereof are able to be freely released from the body organ 36 even if the sealant 34 fully cures or partially cures while still completely or partially filling the reservoir 42. It is also envisioned that prior to the dispensing of the sealant 34 from the jaw members 28, 30, a lubricant (not shown) is applied to the reservoir 42 and/or the inwardly facing surfaces of the jaw members 28, 30 to prevent fully or partially cured sealant 34 from sticking to such surfaces.

Figure 8:
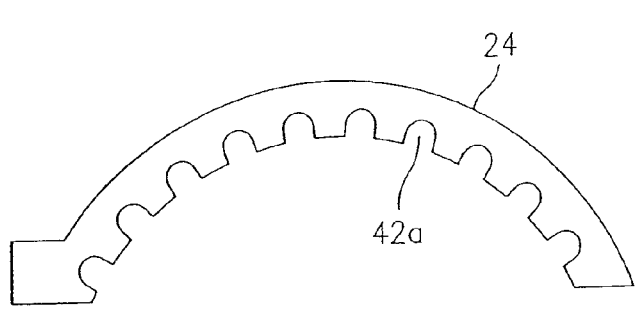
FIGS. 8 and 9 are enlarged cross-sectional views of portions of the end effectors of the extraluminal sealant applicator of FIG. 1, illustrating different types of reservoirs within the end effector.
Figure 8A:
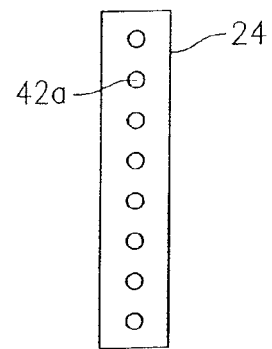
FIGS. 8A and 9A are plan views from the inward side of the end effectors shown in FIGS. 8 and 9, respectively.
Figure 9:
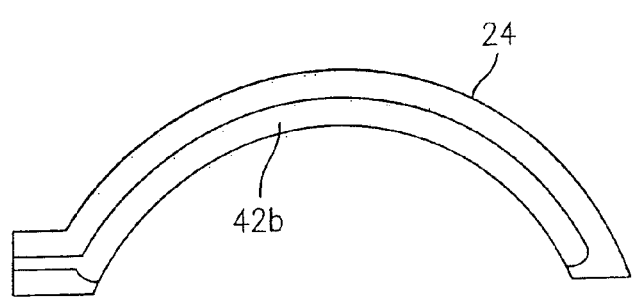
Figure 9A:
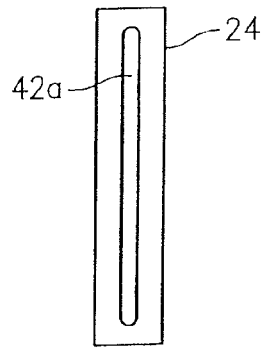

It is envisioned by the present disclosure to have a series of individual reservoirs 42a (see FIGS. 8 and 8A) to be provided along the length of each jaw member 28, 30 and/or, as mentioned above, one elongate reservoir 42b that extends the full length or a portion of the length of the jaw members 28, 30 (see FIGS. 9 and 9A).

It is also envisioned that the apparatus of the present disclosure contains one reservoir 42 disposed towards the proximal portion of each jaw member 28, 30 (not shown). In such an embodiment, a bead of sealant 34 will contact or come close to contacting the proximal portion of the body organ 36 when the end effector 24 is in an open position. When the end effector 24 is moved towards a closed position, each of the jaw members 28, 30 will push/distribute the sealant 34 over the surface of the body organ 36 as the jaw members 28, 30 gradually come into contact with more surface area of the body organ 36.

It is also envisioned that an external means 200 (see FIG. 16) can be used to supply the sealant 34 to the body organ 36 via the end effector 24. The external means 200, such as a syringe, can be used to inject the jaw members 28, 30 with sealant 34 that would be distributed and/or dispensed to the body organ 36 through openings within the jaw members 28, 30.

It is further envisioned that each of the two jaw members 28, 30 can releasably hold a reinforcing pledget (not shown) that is impregnated with sealant. In such an embodiment, each jaw member 28, 30 would have a sealant-impregnated pledget (not shown) disposed thereon. When the jaw members 28, 30 move into a closed position, the pledgets may contact and adhere to the staple line (removing itself from the jaw members 28, 30), thus sealing the site with sealant 34.

Figure 10:
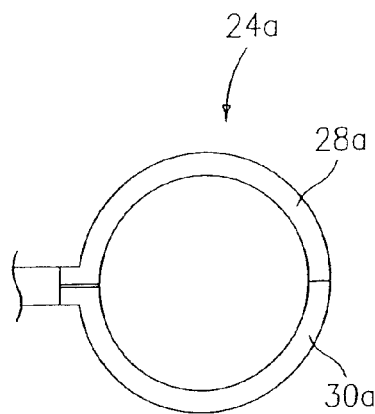
FIGS. 10-14 are cross-sectional views of differently shaped end effectors which can be used with the extraluminal sealant applicator of FIG. 1.
Figure 11:
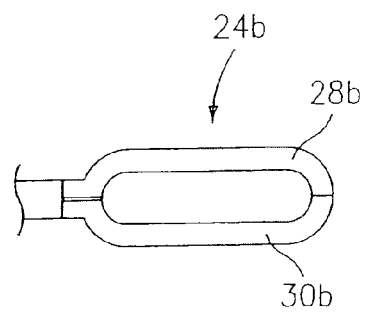
Figure 12:
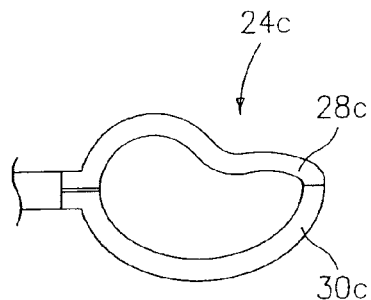

Turning now to FIGS. 10-12, different embodiments of the jaw members 28, 30 are shown and will be described. FIG. 10 shows an end effector 24a including a rigid, arcuate pair of jaw members 28a, 30a. These may be used when the body organ 36 does not significantly deform when pressure is asserted thereto. FIG. 11 depicts an end effector 24b including a rigid, planar pair of jaw members 28b, 30b. This pair may be used when the body organ 36 deforms to a somewhat flattened shape due to the pressure from the stapling surgery or from the pressure associated with the closing of the jaw members 28b, 30b. FIG. 12 illustrates an end effector 24c including a deformable pair of jaw members 28c, 30c. These clamps may be used when the body organ 36 deforms in shape when subjected to the pressure from the surgery and/or the closing of jaw members 28c, 30c. Jaw members 28c, 30c are designed and configured to conform or essentially conform to the resulting curvature that the body organ 36 takes from the pressure of the surgery and/or the pressure of the jaw members 28c, 30c themselves. Surgeons will be able to determine which set of jaw members 28, 30 to use either by past experiences or by trial and error.

Figure 13:
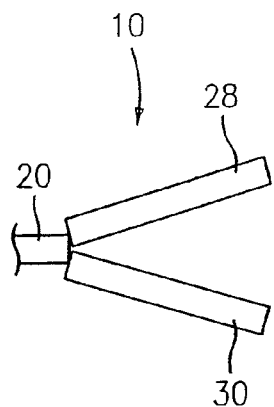
Figure 14:
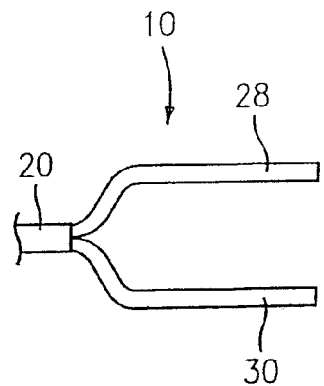

As seen in FIGS. 13 and 14, it is also envisioned for the jaw members 28, 30 to be configured for linear stapling. FIG. 13 depicts the jaw members 28, 30 pivotally attached to the shaft 20 for clamping tissue therebetween. FIG. 14 depicts the jaw members 28, 30 operatively attached to the shaft 20 in a parallel manner for clamping tissue therebetween. These embodiments can be used to apply sealant 34 to tissue that has been joined by linear stapling.

Figure 15:
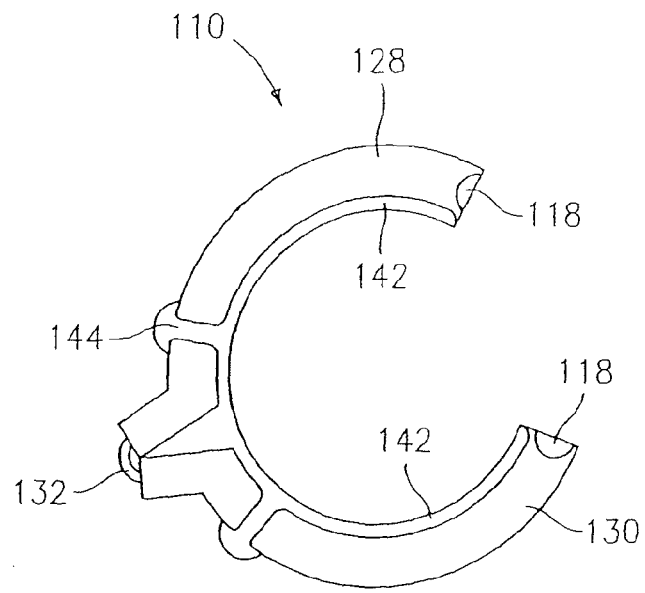
FIG. 15 is a cross-sectional view of a clamp-type extraluminal sealant applicator in accordance with the present disclosure.

Turning now to FIGS. 15-17, an embodiment of an extraluminal sealant applicator in accordance with an embodiment of the present disclosure is generally designated as 110 and is referred to as an applicator clamp. Applicator clamp 110 includes a pair of jaw members 128, 130 connected by a hinge 132. Each jaw member 128, 130 contains at least one port 142 for holding and/or distributing sealant 34 to the staple line 146 and also contains side walls (similar to the side walls 40 of jaw members 28, 30) to help reduce the lateral spread of sealant 34 that has been dispensed. It is envisioned that a locking device 118 can be provided on each of the jaw members 128, 130, opposite the hinge 132 to keep the applicator clamp 110 from opening unintentionally.

The applicator clamp 110 is placed around or adjacent the staple line 146 of body organ 136 and is clamped in a closed position thereto. Once in place, the user distributes sealant 34 to the staple line 146 by activating a sealant applicator device 144 (e.g., a push bulb) disposed on the jaw members 128, 130 or by an external means 200, such as a syringe, as discussed above and illustrated in FIG. 16. After the sealant 34 has been dispensed, the user waits for the sealant 34 to fully or partially cure before removing the applicator clamp 110.

A method of the present disclosure, using any of the apparatus disclosed hereinabove, may be implemented after an anastomosis procedure where a body organ, such as an intestine, bronchus or bowel, is surgically stapled using an end-to-end anastomosis stapler or other suitable device. After such a procedure, the end effector 24 of the apparatus 10 is positioned near the staple line of the tissue, with the end effector 24 in an open position. The user then closes the end effector 24 around the body organ 36 by actuating the end effector operating means 14 of the apparatus 10. After the end effector 24 is closed, the user applies the sealant 34 to the desired tissue by actuating the sealant-applying structure 16. Once the sealant 34 is applied to the tissue, the end effector 24 is maintained in a closed position until the sealant 34 has sufficiently cured. After sufficient curing has taken place, the user may open the end effector 24 by actuating operating means 14 and removing the apparatus 10 from the patient's body.

According to one embodiment of the present disclosure, it is envisioned that an applicator clamp 110 may be provided for surrounding a body organ 136 or tissue and for applying sealant 34 thereto. In this embodiment, a user places the applicator clamp 110 around the body organ 136 and closes the applicator clamp 110. The user then may use a sealant applicator device 144 and/or an external means 200 to apply the sealant 34 to the tissue. The sealant applicator device 144 disposed on the applicator clamp 110 can include a switch, button, slide or the like to release biological sealant from within the applicator clamp 110, through openings within the applicator clamp 110, and onto the tissue. External means 200, such as a syringe, can be used to inject the applicator clamp 110 with a biological sealant solution that would be applied to the tissue through openings within the applicator clamp 110. Side walls may be disposed on the jaw members 128, 130 to confine the sealant 34 to the desired location.

According to an embodiment of the present disclosure, it is envisioned that the end effector 24 may be configured to apply sealant 34 to a surgical site that has been linearly stapled.

It is to be appreciated that the extraluminal sealant applicators and method of the present disclosure may be utilized in a number of other applications and is not limited solely to bowel, intestine or bronchus anastomosis.

While several particular forms of the extraluminal sealant applicators have been illustrated and described, it will also be apparent that various modifications can be made without departing form the spirit and scope of the present disclosure. For example, it is envisioned and within the scope of the present disclosure for a sensor to detect when the sealant has sufficiently cured, and thus when the surgeon should remove the apparatus. It is also envisioned and within the scope of the present disclosure for pins disposed on the edges of the side walls penetrate the outer skin of the body organ, but do not penetrate beyond the outer skin. It is still further envisioned and within the scope of the present disclosure that an adhesive can be applied to the anastomosis site, in lieu of, or in addition to the sealant.

It is further contemplated that each of the extraluminal sealant applicators described herein may be used following surgery performed with an annular surgical anastomosing device, which is capable of approximating, adhering and cutting tissue.

Thus, it should be understood that various changes in form, detail and application of the extraluminal sealant applicators and method of the present disclosure may be made without departing form the spirit and scope of the present disclosure.

What is claimed is:

1. A method of performing an anastomosis of two hollow organs, comprising:
    providing an applicator including an end effector having two jaw members defining an open circle in a closed position and having tissue-contacting surfaces and dispensing apertures directed radially inwardly, and at least one conduit configured for conveying a material to the apertures;
    positioning the jaw members around a junction between the two hollow organs;
    approximating the jaws of the end effector to substantially surround the junction; and
    applying the material to the junction between the two luminal organs via the end effector.

2. The method according to claim 1, wherein the material is selected from the group consisting of a sealant and an adhesive.

3. The method according to claim 2, wherein the material comprising a first material and a second material, the first material and second material forming a two part adhesive.

4. The method according to claim 1, further comprising the step of stapling the organs.

5. The method according to claim 1, further comprising disposing the material in a reservoir, the reservoir being in communication with the apertures.

6. The method according to claim 1, wherein approximating includes moving a handle member from a neutral position to an actuated position.

7. The method according to claim 6, wherein when the handle member moves from the neutral position to the actuated position, the material is pushed from a reservoir through a shaft and dispensed from the apertures.

\* \* \* \* \*